United States Patent
Meier

(10) Patent No.: US 7,164,949 B2
(45) Date of Patent: Jan. 16, 2007

(54) ELECTROSTIMULATOR

(75) Inventor: Jan H. Meier, Spardorf (DE)

(73) Assignee: Biotronik GmbH & Co. KG, Berlin (DE)

(*) Notice: Subject to any disclaimer, the term of this patent is extended or adjusted under 35 U.S.C. 154(b) by 242 days.

(21) Appl. No.: 10/917,876

(22) Filed: Aug. 13, 2004

(65) Prior Publication Data

US 2005/0049645 A1    Mar. 3, 2005

(30) Foreign Application Priority Data

Sep. 2, 2003    (DE)    ................. 103 41 301

(51) Int. Cl.
*A61N 1/37*    (2006.01)
(52) U.S. Cl. ...................................... 607/28
(58) Field of Classification Search .................. 607/28, 607/9, 25; 600/509, 519, 554
See application file for complete search history.

(56) References Cited

U.S. PATENT DOCUMENTS

| | | | |
|---|---|---|---|
| 4,817,605 A |   | 4/1989 | Sholder |
| 5,324,310 A |   | 6/1994 | Greeninger et al. |
| 5,388,586 A | * | 2/1995 | Lee et al. ................... 600/517 |
| 5,443,485 A |   | 8/1995 | Housworth et al. |
| 5,609,611 A | * | 3/1997 | Bolz et al. ................... 607/13 |
| 6,029,088 A | * | 2/2000 | Budgifvars et al. ........... 607/27 |
| 2003/0009200 A1 |   | 1/2003 | Noren et al. |

FOREIGN PATENT DOCUMENTS

EP    0 479 215 A2    4/1992

OTHER PUBLICATIONS

Thomas S. Klitzner and William G. Stevenson, "Effects of Filtering on Right Ventricular Electrograms Recorded from Endocardial Catheters in Humans," PACE, p. 69-77, (Jan. 1990).

* cited by examiner

*Primary Examiner*—Robert Pezzuto
*Assistant Examiner*—Shevon Johnson
(74) *Attorney, Agent, or Firm*—Hahn Loeser & Parks LLP

(57) ABSTRACT

An electrostimulator having electrode connections which are to be connected, at least at times, to a stimulation unit and to a detection unit of the electrostimulator. The stimulation unit is adapted to generate electrostimulation pulses for the stimulation of body tissue and to deliver the electrostimulation pulses to at least one of the electrode connections. The detection unit is adapted to detect successful stimulation of body tissue on the basis of an electrical signal occurring at least one of the electrode connections. The electrostimulator is adapted to record an electrical signal representative of an intracardial electrocardiogram by way of the at least one electrode connection. Arranged between the electrode line connection and the detection unit is a high pass filter with a lower limit frequency of greater than 100 Hz, and the detection unit is adapted to evaluate the high pass-filtered electrical signal.

18 Claims, 4 Drawing Sheets

ELECTROSTIMULATOR

CROSS-REFERENCE TO RELATED APPLICATIONS/INCORPORATION BY REFERENCE

This application claims priority to German patent application serial number 103 41 301.4 filed on Sep. 2, 2003.

TECHNICAL FIELD

Embodiments of the present invention relate to electrostimulators. In particular, certain embodiments of the present invention relate to the aspect of capture detection in electrostimulators such as cardiac pacemakers or the like.

BACKGROUND OF THE INVENTION

Electrostimulators are known in particular in the form of implantable cardiac pacemakers but also cardioverters/defibrillators or in the form of combination units.

Such electrostimulators serve, in particular, to deliver electrostimulation pulses to a myocardium of a heart in order to cause the heart to contract when stimulated by the electrostimulation pulse. For that purpose the electrostimulation pulse must be above the stimulation threshold of the myocardium. As an electrostimulation pulse requires electrical energy which, in particular in the case of an implant, is to be taken from a battery of limited capacity and in the case of an exhausted battery an operation is required, there is basically a need to minimize the energy required for a successful electrostimulation pulse without endangering the success of the electrostimulation procedure. Success with electrostimulation, that is to say the myocardium responding to a stimulation pulse, is usually identified by the English word "capture".

In order to be able to implement a stimulation success checking procedure, cardiac pacemakers frequently have detection units in order to detect successful electrostimulation. Such a detection unit is also referred to as a capture detector.

Further aspects of pacemaker control such as for example setting an adequate stimulation rate or preventing (inhibiting) stimulation pulses in the event of natural contractions of the heart are not in the foreground and are basically known to the man skilled in the art.

SUMMARY OF THE INVENTION

The invention concerns an electrostimulator including electrode connections which are to be connected, at least at times, to an electrostimulation unit and at the same time or alternately to a detection unit of the electrostimulator. In that respect, the stimulation unit is adapted to generate electrostimulation pulses for the stimulation of body tissue and to deliver them to at least one of the electrode connections. The detection unit is adapted to detect successful stimulation of body tissue on the basis of an electrical signal occurring at at least one electrode connection. For that purpose the electrostimulator is adapted to receive an electrical signal representative of an electrocardial electrocardiogram by way of the electrode connection connected to the detection unit.

There is still a need to implement capture detection as soon as possible after delivery of a stimulation pulse so that, in the event of an absence of stimulation success, a backup stimulation pulse with a higher level of energy can be applied to the myocardium without delay.

In accordance with the invention, certain embodiments are achieved by an electrostimulator, wherein arranged between the electrode connection for picking up the electrical signal representative of an intracardial electrocardiogram and the detection unit is a high pass filter with a lower limit frequency >100 Hz and wherein the detection unit is adapted to evaluate the high pass-filtered electrical signal.

Embodiments of the present invention are based on the realization that the higher-frequency constituents of an intracardial electrocardiogram are determined, in particular, by the myocardium which is in the immediate proximity of a sensing electrode, and less by more remote events such that, for example, basically known problems such as crosstalk may be easily suppressed with the arrangement, according to various embodiments of the present invention. In addition, evaluation of the electrocardiogram in the immediate proximity of a corresponding sensing electrode makes it possible for stimulation success to be already detected in a period of a few milliseconds after stimulation pulse delivery.

The electrostimulator may be adapted to record the electrical signal representative of an intracardial electrocardiogram by way of a bipolar electrode configuration. For that purpose, connected to the electrode connection for recording the electrical signal representative of an intracardial electrocardiogram is an at least bipolar electrode line having at least two electrodes for recording electrical potentials at the electrodes. The electrodes may have a low tendency to polarization, that is to say, a low level of post-potential after electrostimulation has occurred. Therefore, electrodes may have a particularly large effective electrode surface area, which may be achieved with a fractal coating.

Embodiments of the present invention are based on the realization that, in the case of a bipolar measuring arrangement, using an electrode line with a tip electrode and a ring electrode for recording the intracardial electrocardiogram, only cardiac activities which originate from a small area of tissue around the electrodes are detected and that such an intracardial electrocardiogram has significant signal components beyond 100 Hz. Conventional and known cardiac pacemakers, in contrast, operate with low pass filters with an upper limit frequency of the order of magnitude of 100 Hz so that usually signal constituents with frequency components above between 50 and 200 Hz are suppressed.

For reducing the post-potentials on the stimulation electrodes, caused by polarization of the stimulation electrodes, there is usually provided a so-called autoshort period, within which the electrodes are short-circuited so that the post-potentials are quickly reduced. During short-circuiting of the stimulation electrodes no intracardial electrocardiogram can be recorded with those electrodes at the stimulation location. The usual autoshort periods of between 10 and 20 ms are too long to be able to detect a stimulation response by means of the intracardial electrocardiogram, with greatly supra-threshold stimulation. Therefore a desired electrostimulator is one which has an autoshort period of less than 5 ms. This may be embodied, in particular in connection with electrodes with a fractal coating which form only low post-potentials by virtue of the large electrode surface area.

In accordance with an embodiment of the present invention, the detection unit is adapted to detect successful stimulation, that is to say capture, and thereupon to produce a corresponding capture signal. This may be effected by the detection unit detecting successful stimulation on the basis of a short-term peak in the electrical signal representative of an intracardial electrocardiogram, more specifically, by threshold value comparison within a defined time window which is started with the delivery of a stimulation pulse.

In connection with a detection unit which produces a capture signal, a desired electrostimulator may be one which has a stimulation control unit which is so connected to the stimulation unit and the detection unit and designed that the stimulation control unit ascertains from the time spacing between the stimulation pulse and the capture signal a stimulation pulse strength signal which determines the strength and, in particular, the amplitude of a following stimulation pulse produced by the stimulation unit. Such an embodiment is based on the realization described in greater detail hereinafter that the period of time between the delivery of a stimulation pulse and the occurrence of stimulation success depends on how greatly above the threshold a respective stimulation pulse is. While, in the case of a greatly supra-threshold stimulation pulse (amplitude for example four times greater than the stimulation threshold) stimulation success already occurs after less than 5 ms, when a slightly supra-threshold stimulation pulse is involved more than 15 ms for example elapse between the stimulation pulse delivery and the occurrence of stimulation success. In that respect, the respective characteristic peak in the intracardially recorded and high pass-filtered electrocardiogram is evaluated as the time at which stimulation success occurs. The realization that it is precisely a high pass-filtered electrocardial electrocardiogram that permits the time at which stimulation success occurs to be accurately ascertained, linked to the realization that the spacing in respect of time between stimulation pulse delivery and the occurrence of stimulation success is characteristic of how greatly the respective stimulation pulse is above the threshold, is used in accordance with the invention to adjust the stimulation pulse strength, that is to say, in particular, the amplitude of a stimulation pulse, in each case to the effect that the stimulation pulse is of precisely the required strength including a safety margin which is possibly desired, without requiring an unnecessarily great amount of energy.

For that purpose, the stimulation control unit may be adapted to compare the spacing in respect of time between the delivery of a stimulation pulse and the subsequent capture signal with a reference time value and to set the stimulation pulse strength signal in such a way that the strength of a respective stimulation pulse decreases with a shorter spacing in respect of time between the delivery of a stimulation pulse and the subsequent capture signal, as long as the spacing in respect of time does not fall below the reference time value. In this connection, the reference time value is preferably set in such a way that it corresponds to a sufficiently supra-threshold stimulation effect. Setting of the reference time value can be effected for example after implantation of an electrostimulator by the physician in charge, but also in an autonomous learning phase in which the electrostimulator delivers a plurality of stimulation pulses of infra-threshold and supra-threshold strength and measures the longest time which elapses between stimulation pulse delivery and the occurrence of stimulation success. That time corresponds to the latency time between stimulation pulse delivery and occurrence of stimulation success, which is to be measured when the stimulation pulse strength precisely corresponds to the stimulus threshold. For safety reasons, the reference value is set to be slightly shorter than the latency time ascertained in that way.

In addition the stimulation control unit may be so designed that, in the event of stimulation success failing to occur within a predetermined time window after delivery of the stimulation pulse, the stimulation control unit triggers a backup stimulation pulse which is of greater strength than the previously unsuccessful stimulation pulse. Here, too, evaluation of the high pass-filtered intracardial electrocardiogram permits very fast triggering of a backup stimulation pulse subsequently to a preceding unsuccessful stimulation procedure.

In addition, an electrostimulator may be desired, which is provided with a telemetry unit with which values in respect of the spacing in respect of time between a stimulation pulse and the stimulation success which thereupon occurs can be communicated into an external unit. Such values may be communicated as pairs of values jointly with the associated stimulation pulse strength. Emission of the time spacing values and optionally the associated stimulation pulse strengths may be implemented in real time. Alternatively, it is also possible to provide a memory in which a plurality of such values are stored and are emitted either at a prescribed moment in time or in response to an enquiry.

BRIEF DESCRIPTION OF SEVERAL VIEWS OF THE DRAWINGS

The invention will now be described in greater detail by means of embodiments by way of example with reference to the accompanying drawings in which.

DETAILED DESCRIPTION OF THE INVENTION

Figure 1:
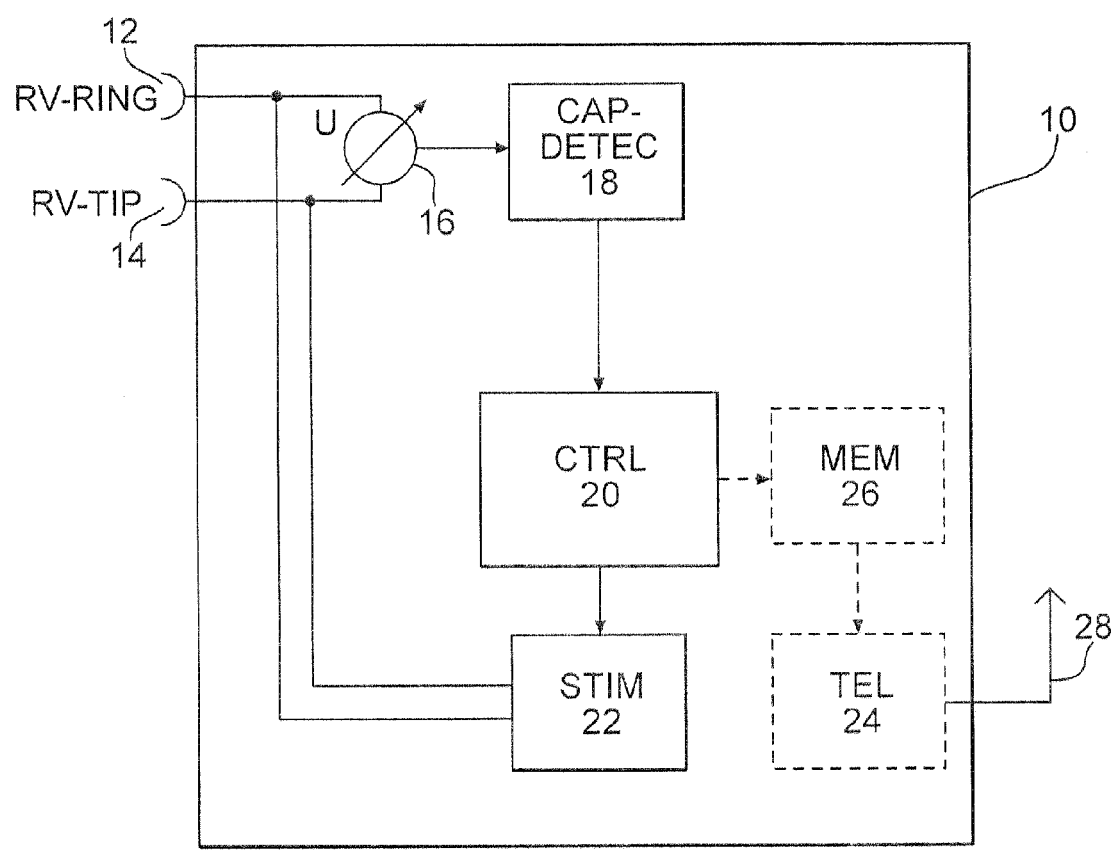
FIG. 1 is a diagrammatic view of an electrostimulator, in accordance with an embodiment of the present invention.

FIG. 1 is a diagrammatic view of an electrostimulator 10 which in particular may be an implantable cardiac pacemaker but also a cardioverter/defibrillator or both, in accordance with various embodiments of the present invention.

The electrostimulator 10 is provided at least with the two electrode connections 12 and 14 shown in FIG. 1 for a right-ventricular ring electrode and a right-ventricular tip electrode. Instead of a ring electrode and a tip electrode, it is also possible to provide two ring electrodes. Arranging the electrodes in the right ventricle corresponds to the most frequent situation of use. An arrangement in a coronary vein which branches from the coronary sinus, that is to say associated with the left ventricle, or also on the left atrium, is also possible.

In order to measure potentials at the electrodes, the arrangement has a voltage measuring unit 16 which is connected to the electrode connections and which passes a respectively ascertained voltage signal to a capture detector 18. The capture detector 18 serves as the detection unit in accordance with various embodiments of the present invention.

A high pass filter (not shown in greater detail in FIG. 1) with a lower limit frequency of $\geq$100 Hz is either connected on the input side of the voltage measuring unit 16 or is provided between the voltage measuring unit 16 and the capture detector 18, in accordance with various embodiments of the present invention.

Figure 2:
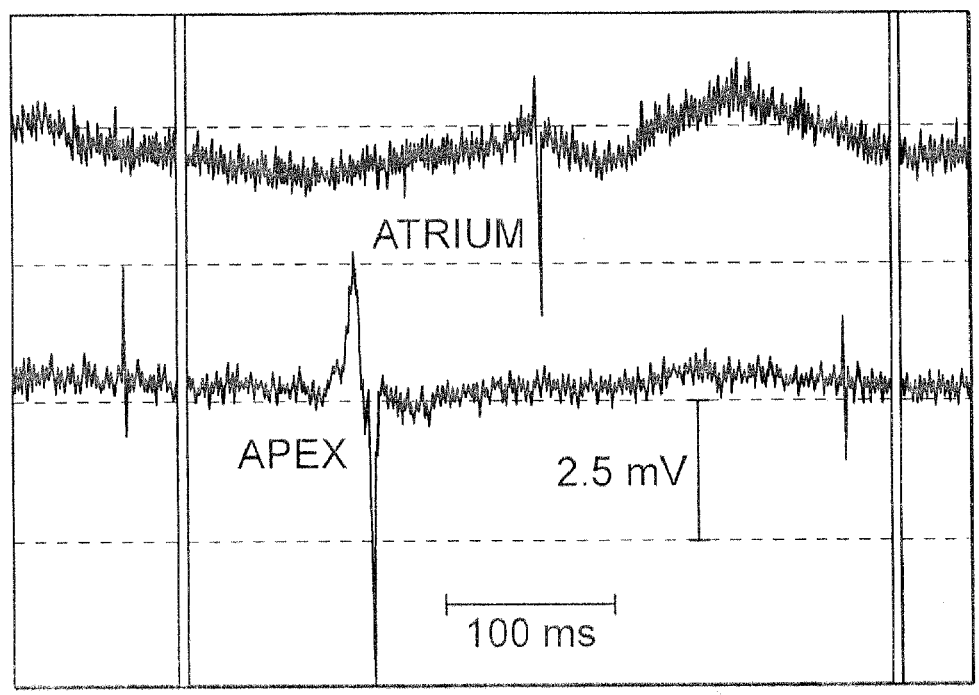
FIG. 2 shows an example of an intracardial electrocardiogram which represents natural heart contractions, in accordance with an embodiment of the present invention.

The capture detector 18 is adapted to evaluate the high-frequency intracardial electrocardiogram. Examples of such electrocardiograms in the case of natural and stimulated contraction of the heart are shown in FIG. 2 and FIG. 3 respectively.

Figure 3:
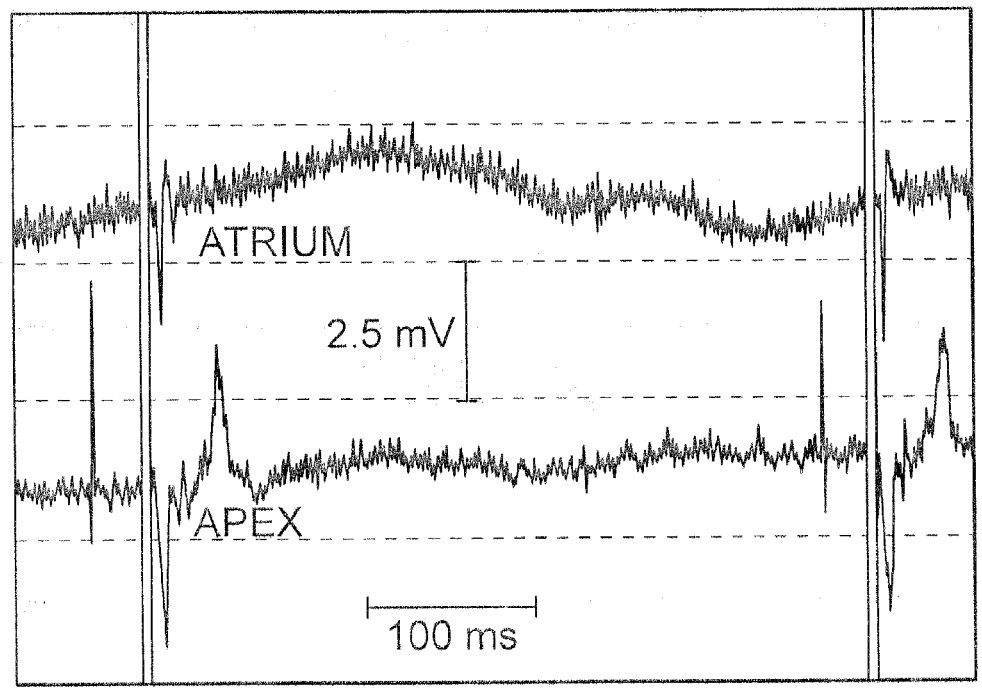
FIG. 3 shows an example of an intracardial electrocardiogram which represents tissue potentials after successful electrostimulation, in accordance with an embodiment of the present invention.

The capture detector 18 is adapted to detect a peak which is characteristic of successful stimulation, in the high pass-filtered electrocardiogram, as is shown in FIG. 3. The capture detector is further adapted to detect such peaks which occur within a predetermined time window after the delivery of a stimulation pulse. For that purpose the capture detector is provided with a timer which is started as soon as a stimulation pulse is delivered.

The capture detector 18 is further adapted by means of the timer to determine the time spacing which exists between the delivery of a respective stimulation pulse and the occurrence of stimulation success. The capture detector derives, from the time spacing, a time spacing signal which the capture detector passes to a stimulation control unit 20.

In addition, the capture detector 18 generates a capture signal when the capture detector 18 detects stimulation success on the basis of the characteristic peak, within the predetermined time window, in the high pass-filtered intracardial electrocardiogram. In the reverse case, if no stimulation success is ascertained within the time window, the capture detector 18 generates a non-capture signal. Both the capture signal and also the non-capture signal are passed by the capture detector 18 to the stimulation control unit 20.

In the case of a non-capture signal on the part of the capture detector 18, the stimulation control unit 20, without delay, triggers a backup stimulation pulse. For that purpose, the stimulation control unit 20 is connected to a stimulation unit 22. The backup stimulation pulse is of a greater strength, in particular a greater amplitude, than the previously unsuccessful stimulation pulse. In the case of a capture signal on the part of the capture detector 18, the stimulation control unit 20 evaluates the time spacing signal and ascertains whether, and possibly also by how much, the spacing in respect of time between the delivery of a stimulation pulse and the occurrence of stimulation success (capture signal) is shorter than a previously stored reference time value. As soon as the spacing in respect of time, afforded by the time spacing signal, is shorter than the reference time value, the stimulation control unit 20 generates a stimulation pulse strength signal which causes the stimulation unit 22 to deliver the next following stimulation pulse at a lower strength, that is to say, of smaller amplitude.

By virtue of the above-discussed physiological relationships, the consequence of this is that the latency time which is subsequent to the next following stimulation pulse is prolonged until stimulation success occurs. If the latency time is sufficiently long and corresponds to the reference time value, the stimulation control unit 20 does not cause any further reduction in the stimulation pulse strength. In that way, it is possible to implement elegant regulation of the stimulation pulse strength which, unlike the situation with the state of the art, does not rely on regularly producing infra-threshold, that is to say, ineffective stimulation pulses.

Further properties of the electrostimulator of FIG. 1, which are not further illustrated in the diagrammatic drawing and which are known in principle to the man skilled in the art, are afforded for example by a short-circuit switch for short-circuiting the two electrode connections 12 and 14 in order to implement the so-called autoshort procedure. In the electrostimulator, according to various embodiments of the presens invention, the short-circuit switch is closed for a maximum of 5 ms after the delivery of a stimulation pulse in order to be able to record an intracardial electrocardiogram directly following those 5 ms. For that purpose, the short-circuit switch has to be opened again, that is to say, the two electrode connections 12 and 14 are not short-circuited.

FIG. 1 shows, in broken line, an optional telemetry unit 24 which is connected by way of a memory 26 to the stimulation control unit 20. The telemetry unit 24 serves for telemetric communication of time spacing signals stored in the memory 26 and associated stimulation pulse strengths in paired relationship to an external unit. The telemetry unit 24 is connected to an antenna 28 indicated in FIG. 1.

Analysis of the time spacing values and the associated stimulation amplitudes may then also be effected in an external unit in order, for example, to ascertain a suitable reference time value. This makes it possible for the stimulation control unit, which is internal to the electrostimulator, to be of a simpler design than as described hereinbefore.

FIG. 2 shows an intracardial electrocardiogram of an intrinsic event as is involved with a natural contraction of a heart. The intracardial electrocardiogram is high pass-filtered with a first-order high pass filter with a limit frequency of 500 Hz. The two vertical bars represent periods in which the corresponding heart was not stimulated effectively with a pacemaker and which were therefore excluded from the representation.

Recording of the intracardial electrocardiogram is effected with a bipolar measuring arrangement in which the ring electrode and the tip electrode of a single electrode line are used for recording the tissue potentials. The recorded tissue potentials were subjected to high pass filtering which resulted in the sharp signal peaks shown in FIG. 2. Those signal peaks are involved in a rise phase of a local action potential.

The bipolar measuring arrangement ensures that only electrical activities from the most closely adjacent environment of the electrodes are measured. Activities of other chambers of the heart or the skeletal muscles are greatly suppressed. This reduces both possible crosstalk perception (i.e., perception of activities of other chambers of the heart than that in which the measurement procedure is conducted) and also the detection of muscular activities. This effect is further re-enforced by high pass filtering of the signal. In a bipolar measuring arrangement, the curve in respect of the frequency response is displaced in the direction of lower frequencies to a correspondingly greater degree, the greater the measuring spacing becomes. With an increasing distance from the measurement location, higher frequency components are reduced to a greater degree than low-frequency signal components. Therefore, crosstalk and the perception of skeletal muscle activities are reduced still further by high pass filtering of the measurement signal, than is already afforded by the bipolar measuring arrangement.

Immediately after the delivery of stimulation pulses, a cardiac pacemaker usually short-circuits the stimulation electrodes (during a so-called autoshort period) in order to allow charges which have accumulated during the stimulation procedure on the electrode surface to flow away. The duration of that autoshort period is usually between 10 and 20 ms so that the rise phase of action potentials which are attributed to a stimulation pulse cannot be perceived. In accordance with an embodiment of the present invention, therefore, the cardiac stimulator is adapted to switch on an autoshort period of not more than 5 ms. In order, nonetheless, to minimize post-potentials on the electrodes, the electrodes are provided with an active surface area which is as large as possible and which is achieved by a fractal coating.

FIG. 3 shows a high pass-filtered intracardial electrocardiogram in reaction to a stimulation pulse. A sharp negative peak characterizing stimulation success follows the stimulation pulse within 15 ms.

Figure 4:
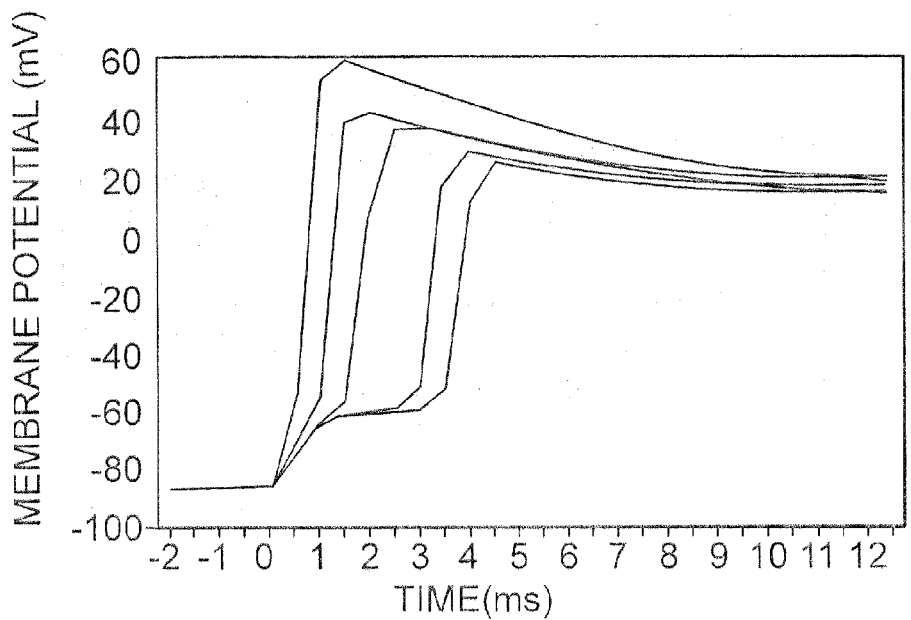
FIG. 4 shows action potentials of the myocardium following successful electrostimulation for various stimulation strengths, in accordance with an embodiment of the present invention.

FIG. 4 shows the typical pattern of action potentials of the cell membranes of the myocardium following electrostimulation. The rising phases of the pattern of the action potentials can be clearly seen. The action potentials with the rise phase which is furthest to the left are due to stimulation pulses of greater strength (higher voltage, energy), while the action potential patterns which are further to the right are due to stimulation with weaker stimulation pulses. The action potential patterns are similar. In the case of stimulation pulses near the stimulus threshold of the myocardium (slightly supra-threshold), however, it can be seen that the membrane potential initially remains for a few milliseconds at a slightly increased plateau before the actual rise phase of the action potential pattern begins.

Figure 5:
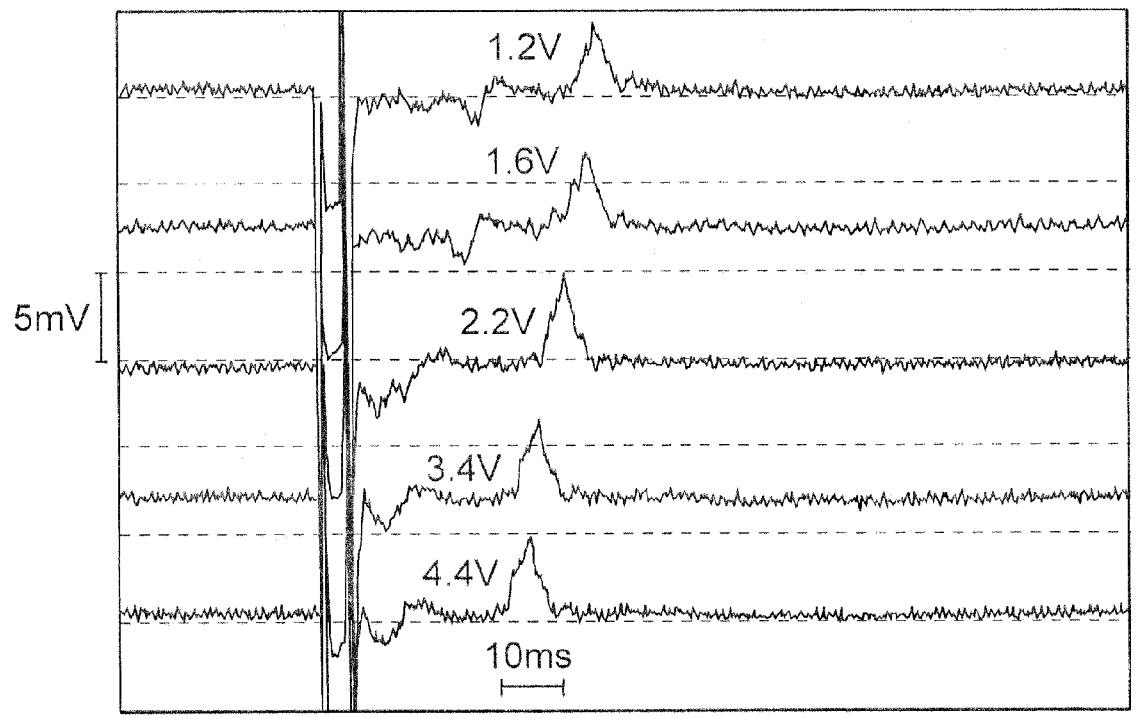
FIG. 5 shows various electrocardiograms which represent the stimulus response of the myocardium upon stimulation with various stimulation strengths, in accordance with an embodiment of the present invention.

The rise phase of the action potential pattern is reflected in a peak in a corresponding, high pass-filtered intracardial electrocardiogram. Electrocardiograms of that kind for various stimulation pulse strengths are shown in FIG. 5. It can be seen that, the smaller the stimulation pulse, the correspondingly later is the occurrence of the peak in the intracardial electrocardiogram. The time shift between the occurrence of a peak in the intracardial electrocardiogram for a stimulation pulse which is just supra-threshold and one which is four times as great as the stimulus threshold of the myocardium is between about 10 and 15 ms.

The position of a peak in the intracardial electrocardiogram is, therefore, an indicator of the amount by which the amplitude of a stimulation pulse is above the stimulus threshold. In accordance with an embodiment of the present invention, therefore, the electrostimulator is adapted to set the strength of a stimulation pulse in dependence on the period of time which elapses between the delivery of a stimulation pulse and the occurrence of the peak in the high pass-filtered intracardial electrocardiogram. If that period of time is very short, for example less than between 5 and 10 ms, the strength of the stimulation pulse can be reduced without endangering stimulation success for the next stimulation pulse. This is in contrast to other known cardiac pacemakers with a so-called auto-capture algorithm in which the stimulation pulse amplitude is usually reduced until it is no longer possible to detect a stimulation pulse. It is only then that the stimulation pulse amplitude is raised again slightly. Accordingly, known auto-capture algorithms usually accept a lack of stimulation success.

Therefore, in an initial learning phase, in accordance with an embodiment of the present invention, the electrostimulator automatically sets a reference time value for the spacing in respect of time between stimulation pulse delivery and the occurrence of the stimulus response, below which successful stimulation is regularly ensured. During the next following period of operation, the stimulation control unit of the cardiac pacemaker regularly sets the simulation strength such that the respective measured time value is slightly below or corresponds to the reference time value.

Figure 6A:
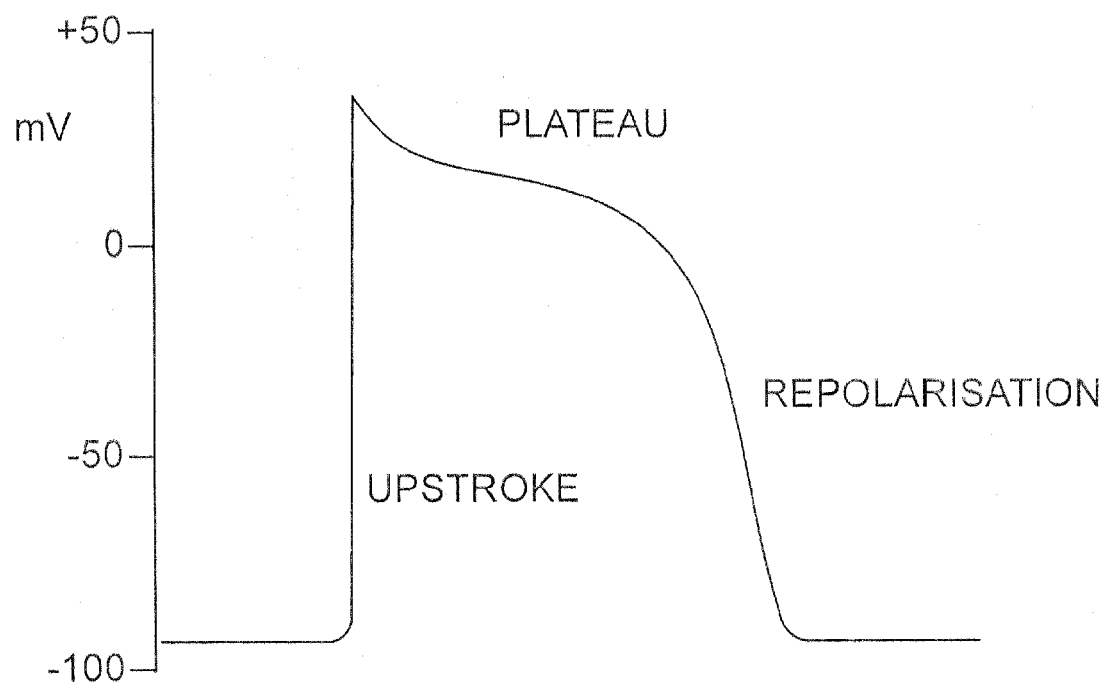
FIG. 6a shows a diagrammatic representation of an action potential, in accordance with an embodiment of the present invention.
Figure 6B:
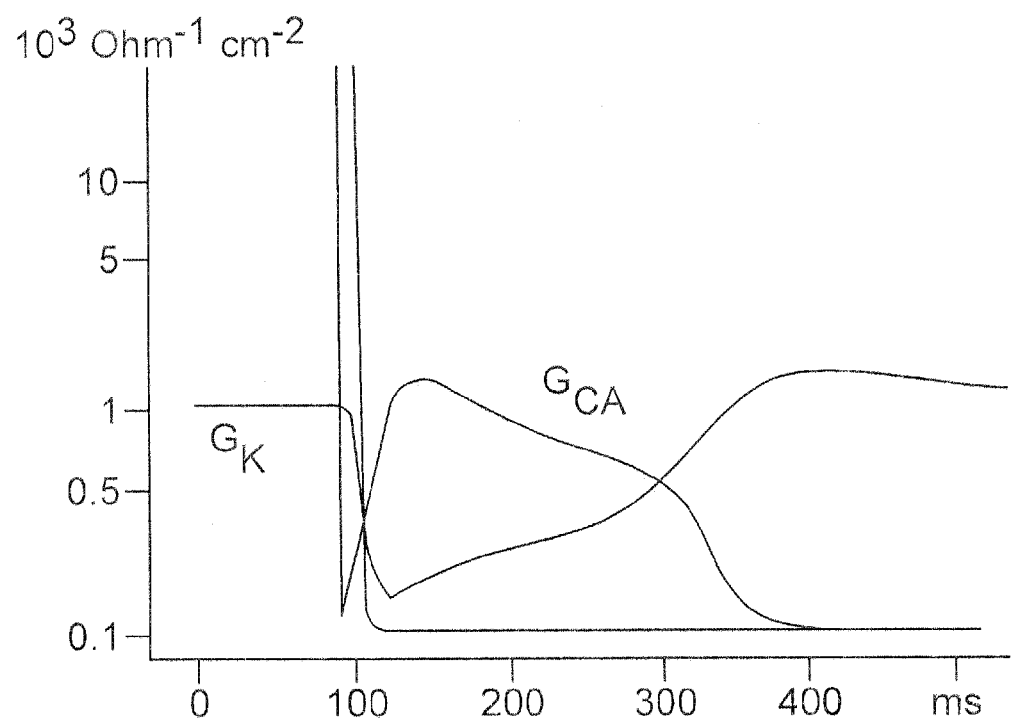
FIG. 6b shows a representation of the ion conductivity and the ion currents which lead to the action potential configuration shown in FIG. 6a, in accordance with an embodiment of the present invention.

FIGS. 6a and 6b serve to further describe the behavior of the myocardium following electrostimulation, in accordance with an embodiment of the present invention.

What is claimed is:

1. An electrostimulator comprising electrode connections which are to be connected at least at times to a stimulation unit and to a detection unit of the electrostimulator, wherein the stimulation unit is adapted to generate electrostimulation pulses for the stimulation of body tissue and to deliver the electrostimulation pulses to at least one of the electrode connections, and wherein the detection unit is adapted to detect successful stimulation of body tissue on the basis of an electrical signal occurring at at least one of the electrode connections, and wherein the electrostimulator is adapted to record an electrical signal representative of an intracardial electrocardiogram by way of said at least one electrode connection, and wherein arranged between the at least one electrode connection and the detection unit is a high pass filter with a lower limit frequency of greater than 100 Hz, and wherein the detection unit is adapted to evaluate the high pass-filtered electrical signal.

2. The electrostimulator as set forth in claim 1 wherein the electrostimulator is adapted to record the electrical signal representative of an intracardial electrocardiogram by way of a bipolar electrode configuration.

3. The electrostimulator as set forth in claim 2 wherein connected o the electrode connection for recording the electrical signal representative of an intracardial electrocardiogram is an at least bipolar electrode line which has at least two electrodes for recording electrical potentials at the electrodes, wherein the electrodes have a low degree of polarization.

4. The electrostimulator as set forth in claim 3 wherein the electrodes include a fractal coating.

5. The electrostimulator as set forth in claim 4 wherein the electrostimulator includes an autoshort device for short-circuiting stimulation electrodes, which is adapted to short-circuit the electrodes for not longer than 5 milliseconds.

6. The electrostimulator as set forth in claim 5 wherein the detection unit is adapted to detect successful stimulation (capture) and to produce a capture signal.

7. The electrostimulator as set forth in claim 6 wherein the detection unit is adapted to detect successful stimulation on the basis of a short-term peak in the electrical signal representative of an intracardial electrocardiogram.

8. The electrostimulator as set forth in claim 7 wherein the detection unit is adapted to detect a short-term peak in the electrical signal representative of an intracardial electrocardiogram within a defined time window which is started with the delivery of a stimulation pulse.

9. The electrostimulator as set forth in claim 8 further comprising a stimulation control unit which is so connected to the stimulation unit and the detection unit and adapted such that the stimulation control unit ascertains from the spacing in respect of time between a stimulation pulse and a capture signal a stimulation pulse strength signal which determines the strength of a following stimulation pulse produced by the stimulation unit.

10. The electrostimulator as set forth in claim 9 wherein the stimulation control unit is adapted to compare the spacing in respect of time between the delivery of a stimulation pulse and the following capture signal to a reference time value and to set the stimulation pulse strength signal in such a way that the strength of a stimulation pulse decreases with a shorter spacing in respect of time between the delivery of a stimulation pulse and the following capture signal as long as the spacing in respect of time does not fall below the reference time value.

11. The electrostimulator as set forth in claim 10 wherein the reference time value is set in such a way that the reference time value corresponds to a sufficiently suprathreshold stimulation.

12. The electrostimulator as set forth in claim 9 wherein the stimulation control unit is adapted in the event of absence of a capture signal within a predetermined time window after delivery of a stimulation pulse to trigger a backup stimulation pulse of greater strength.

13. The electrostimulator as set forth in claim 12 further comprising a telemetry unit which is connected to the detection unit and adapted to send a time spacing signal corresponding to the spacing in respect of time between a stimulation pulse and a capture signal to an external unit.

14. The electrostimulator as set forth in claim 13 further comprising a memory for storing one or more values of the time spacing signal, which is connected to the detection unit and the telemetry unit.

15. The electrostimulator as set forth in claim 6 further comprising a stimulation control unit which is so connected to the stimulation unit and the detection unit and adapted such that the stimulation control unit ascertains from the spacing in respect of time between a stimulation pulse and a capture signal a stimulation pulse strength signal which determines the strength of a following stimulation pulse produced by the stimulation unit.

16. The electrostimulator as set forth in claim 6 further comprising a telemetry unit which is connected to the detection unit and adapted to send a time spacing signal corresponding to the spacing in respect of time between a stimulation pulse and a capture signal to an external unit.

17. The electrostimulator as set forth in claim 1 wherein the detection unit is adapted to detect successful stimulation (capture) and to produce a capture signal.

18. An electrostimulator comprising electrode connections which are to be connected at least at times to a stimulation unit and to a detection unit of the electrostimulator, wherein the stimulation unit is adapted to generate electrostimulation pulses for the stimulation of body tissue and to deliver the electrostimulation pulses to at least one of the electrode connections, and wherein the detection unit is adapted to detect successful stimulation of body tissue on the basis of an electrical signal occurring at at least one of the electrode connections, and wherein the electrostimulator is adapted to record an electrical signal representative of an intracardial electrocardiogram by way of said at least one electrode connection, and wherein arranged between the at least one electrode connection and the detection unit is a high pass filter with a lower limit frequency of greater than 100 Hz, and wherein the detection unit is adapted to evaluate the high pass-filtered electrical signal, and wherein the electrostimulator includes an autoshort device for short-circuiting stimulation electrodes, which is adapted to short-circuit the electrodes for not longer than 5 milliseconds.

* * * * *